(12) United States Patent
Conroy et al.

(10) Patent No.: US 11,620,554 B2
(45) Date of Patent: Apr. 4, 2023

(54) ELECTRONIC CLINICAL DECISION SUPPORT DEVICE BASED ON HOSPITAL DEMOGRAPHICS

(71) Applicant: KONINKLIJKE PHILIPS N.V., Eindhoven (NL)

(72) Inventors: Bryan Conroy, Garden City South, NY (US); Cristhian Mauricio Potes Blandon, Salem, NH (US); Minnan Xu, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 208 days.

(21) Appl. No.: 16/323,802

(22) PCT Filed: Aug. 1, 2017

(86) PCT No.: PCT/EP2017/069365
§ 371 (c)(1),
(2) Date: Feb. 7, 2019

(87) PCT Pub. No.: WO2018/029028
PCT Pub. Date: Feb. 15, 2018

(65) Prior Publication Data
US 2019/0164648 A1 May 30, 2019

Related U.S. Application Data

(60) Provisional application No. 62/371,886, filed on Aug. 8, 2016.

(51) Int. Cl.
*G06N 7/00* (2006.01)
*G16H 50/70* (2018.01)
(Continued)

(52) U.S. Cl.
CPC .............. *G06N 7/005* (2013.01); *G06N 3/02* (2013.01); *G16H 10/60* (2018.01); *G16H 50/20* (2018.01);
(Continued)

(58) Field of Classification Search
CPC .......... G06N 7/005; G06N 3/02; G06N 20/00; G16H 10/60; G16H 50/70; G16H 50/20; G16H 50/30
See application file for complete search history.

(56) References Cited

U.S. PATENT DOCUMENTS

2006/0248031 A1* 11/2006 Kates ............... G16H 50/20
706/25
2015/0206067 A1 7/2015 Abu-Mostafa et al.
(Continued)

FOREIGN PATENT DOCUMENTS

WO WO-2009076551 A2 * 6/2009 ............. G16B 40/00
WO 2016094330 A2 6/2016

OTHER PUBLICATIONS

Wen, Robust Learning under Uncertain Test Distributions, 2013, Library and Archives Canada, pp. 1-46. (Year: 2013).*
(Continued)

*Primary Examiner* — Christopher L Gilligan (57) ABSTRACT

An electronic clinical decision support (CDS) device (10) employs a trained CDS algorithm (30) that operates on values of a set of covariates to output a prediction of a medical condition. The CDS algorithm was trained on a training data set (22). The CDS device includes a computer (12) that is programmed to provide a user interface (62) for completing clinical survey questions using the display and the one or more user input devices. Marginal probability distributions (42) for the covariates of the set of covariates are generated from the completed clinical survey questions. The trained CDS algorithm is adjusted for covariate shift (Continued)

using the marginal probability distributions. A prediction of the medical condition is generated for a medical subject using the trained CDS algorithm adjusted for covariate shift (50) operating on values for the medical subject of the covariates of the set of covariates.

12 Claims, 3 Drawing Sheets

(51) Int. Cl.
    *G06N 3/02*       (2006.01)
    *G16H 50/20*     (2018.01)
    *G16H 10/60*     (2018.01)
    *G16H 50/30*     (2018.01)
    *G06N 20/00*     (2019.01)

(52) U.S. Cl.
    CPC ............. *G16H 50/70* (2018.01); *G06N 20/00* (2019.01); *G16H 50/30* (2018.01)

(56) References Cited

U.S. PATENT DOCUMENTS

| | | | |
|---|---|---|---|
| 2016/0188822 A1* | 6/2016 | Ryan | G16H 50/20 705/3 |
| 2016/0210435 A1* | 7/2016 | Neumann | G16H 50/50 |
| 2016/0232324 A1* | 8/2016 | Liu | G16H 50/20 |
| 2016/0321748 A1* | 11/2016 | Mahatma | G06Q 40/08 |
| 2017/0068789 A1* | 3/2017 | Dalton | G16H 50/20 |
| 2017/0083670 A1* | 3/2017 | Kosaka | G16H 70/40 |

OTHER PUBLICATIONS

Tortajada et al., Incremental Gaussian Discriminant Analysis based on Graybill and Deal weighted combination of estimators for brain tumour diagnosis, Mar. 4, 2011, Journal of Biomedical Information, pp. 677-687. (Year: 2011).*

Gong, et al., "Instance Weighting for Patient-Specific Risk Stratification Models", Proceedings of the 21th ACM SIGKDD International Conference on Knowledge Discovery and Data Mining, pp. 369-378 (Abstract).

"Adventures in Data Land", Real simple covariate shift correction, Nov. 27, 2015, 2 pages (Abstract).

Kumar, S. et al., "Learning Under Data Shift for Domain Adaptation: A Model-Based Co-clustering Transfer Learning Solution". School of Engineering and Computer Science. Springer International Publishing Switzerland 2016, pp. 43-54.

Weiss, K. et al., "A survey of transfer learning". Journal of Big Data (2016) 3:9.

* cited by examiner

ELECTRONIC CLINICAL DECISION SUPPORT DEVICE BASED ON HOSPITAL DEMOGRAPHICS

CROSS-REFERENCE TO PRIOR APPLICATIONS

This application is the U.S. National Phase application under 35 U.S.C. § 371 of International Application No. PCT/EP2017/069365, filed on Aug. 1, 2017, which claims the benefit of Provisional Application Ser. No. 62/371,886, filed Aug. 8, 2016. These applications are hereby incorporated by reference herein, for all purposes.

FIELD

The following relates generally to the electronic clinical decision support (CDS) arts, clinical arts, and the like.

BACKGROUND

An electronic clinical decision support (CDS) device comprises a computer or other electronic processor programmed to provide clinical information based on input information about a medical subject. The input information comprises a set of quantifiable covariates (which may be binary-valued in some cases) such as laboratory test results, radiology study findings, demographic information about the medical subject (e.g. age, gender, et cetera), body weight, or so forth. Machine learning is applied to the set of covariates to produce a predictor of the form P(y|x) where x is a vector whose elements store values of the covariates for a subject, and y is the value of the medical condition to be predicted (which again may be binary-valued in some cases, e.g. "1" indicating the patient has the medical condition, "0" indicating the patient does not; alternatively, $y_i$ may be real-valued or have some other type of value, e.g. $y_i$ may be a cancer stage that may assume any one of several possible values).

An electronic CDS device is typically constructed by collecting training samples denoted herein without loss of generality as $(x_i, y_i)$, i=1, . . . , n where n is the number of training samples (i.e. the number of training subjects), $x_i$ is the vector of covariate values for the $i^{th}$ training subject, and $y_i$ is the (known) value of the medical condition for the $i^{th}$ training subject. The set of training data is preferably large, and should be sufficiently diverse to represent the full range of medical subjects to which the electronic CDS device is expected to be applicable. The collected set of training samples is used to train a CDS algorithm by machine learning, such that the algorithm predicts the value of the medical condition y with good accuracy given an input set of values x for the set of covariates. For example, the training may optimize the CDS algorithm to minimize the normalized sum-squared error $$\frac{1}{N}\sum_{i=1}^{N}(\hat{y}_i - y_i)^2$$

where $\hat{y}_i$ is the prediction for the $i^{th}$ training subject.

In a typical commercial implementation, the electronic CDS is constructed by a vendor using a set of training samples acquired from various sources. The samples are preferably anonymized to maintain patient confidentiality (e.g. to comply with HIPAA requirements in the United States). The constructed electronic CDS then may be marketed to various medical institutions, such as hospitals, hospital networks, or the like, for use in providing clinical diagnostic assistance.

SUMMARY

In one disclosed aspect, an electronic clinical decision support (CDS) device employs a trained CDS algorithm that operates on values of covariates of a set of covariates to output a prediction of a medical condition. The trained CDS algorithm was trained on a training data set of training samples. The CDS device comprises a computer including a display and one or more user input devices. The computer is programmed to adjust the trained CDS algorithm for covariate shift by computing covariate shift adjustment weights for the training samples of the training data set using marginal probability distributions for the covariates of the set of covariates and performing update training on the training data set with the training samples weighted by the covariate shift adjustment weights. The computer is further programmed to generate a prediction of the medical condition for a medical subject by applying the trained CDS algorithm adjusted for covariate shift to values for the medical subject of the covariates of the set of covariates, and to display the generated prediction of the medical condition for the medical subject on the display.

In another disclosed aspect, an electronic CDS device employs a trained CDS algorithm that operates on values of covariates of a set of covariates to output a prediction of a medical condition. The trained CDS algorithm was trained on a training data set of training samples. The CDS device comprises a computer including a display and one or more user input devices. The computer is programmed to provide a user interface for completing clinical survey questions using the display and the one or more user input devices, to generate marginal probability distributions for the covariates of the set of covariates from the completed clinical survey questions, and to adjust the trained CDS algorithm for covariate shift using the marginal probability distributions. The computer is further programmed to generate a prediction of the medical condition for a medical subject using the trained CDS algorithm adjusted for covariate shift operating on values for the medical subject of the covariates of the set of covariates.

In another disclosed aspect, an electronic CDS method employs a CDS algorithm that operates on values of covariates of a set of covariates to output a prediction of a medical condition. In the CDS method, the CDS algorithm is trained on a training data set of training samples using a first computer. After the training, CDS operations are performed using a second computer different from the first computer. The CDS operations include: adjusting the trained CDS algorithm for covariate shift using marginal probability distributions for the covariates of the set of covariates; generating a prediction of the medical condition for a medical subject by applying the trained CDS algorithm adjusted for covariate shift to values for the medical subject of the covariates of the set of covariates; and displaying the generated prediction of the medical condition for the medical subject on a display.

One advantage resides in providing a more accurate electronic clinical decision support (CDS) device tailored to the population served by a specific hospital or other specific medical institution.

Another advantage resides in providing this improved accuracy without requiring collection of training samples representing medical subjects served by the specific medical institution or organization.

Another advantage resides in providing this improved accuracy leveraging available or readily collected statistics that do not contain potentially personally identifying information (PII).

Another advantage resides in providing this improved accuracy in a computationally efficient manner thereby improving the electronic CDS device itself by enabling it to be implemented with reduced memory and/or reduced computational power.

Another advantage resides in providing an electronic CDS device that may be efficiently updated to adjust for changing population served by the specific hospital or other specific medical institution or organization.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention. Unless otherwise noted, the drawings are diagrammatic and are not to be construed as being to scale or to illustrate relative dimensions of different components.

DETAILED DESCRIPTION

A problem that can arise with a commercial CDS device is that the CDS algorithm may have been trained on a training samples set (i.e. training population) that is statistically different from the population of patients encountered by the customer (e.g. a hospital purchasing and using the CDS device to assist in diagnosing patients in a clinical setting). These differences may be due to any of a wide range of factors: different age demographics; different ethnic demographics; different income levels (which can indirectly impact medical condition statistics due to differing levels of preventative care); different geographical regions; different target populations (e.g. an urban hospital may serve a population with different statistics than a rural hospital); and so forth.

It might be thought that such a difference in populations should not be problematic, so long as the training set used to develop the CDS device at the vendor is sufficiently large and diverse to encompass a statistically significant number of samples representative of the population served by the customer. However, even assuming the CDS device vendor was successful in gathering and training on a suitably large and diverse training set, it has been found that due to the empirical nature of a trained predictor of the form $y=f(x)$ where x is the covariate vector and $f( \ldots )$ is the trained predictor, the actual performance can be degraded if the covariate statistics encountered in the inference (e.g. customer) population deviate significantly from the covariate statistics of the training population (e.g. relied upon by the CDS device vendor). This problem is sometimes referred to as "covariate shift", because the statistics of the covariates x have changed or "shifted".

Covariate shift can be addressed by acquiring data from the inference distribution (e.g. customer) in order to model the difference between training and inference distributions. However, in the context of a CDS device this may be an unsatisfactory approach. Generating the inference distribution entails collecting patient data from the customer (e.g. hospital), which has a number of drawbacks. The customer patient data may be analyzed by the CDS device vendor in order to provide a CDS device product that is tailored to the customer—but the hospital may be unwilling to provide its sensitive patient data to the CDS device vendor due to concerns about violating patient privacy laws (e.g. HIPAA in the United States). The data may be anonymized before being delivered to the CDS device vendor, but this requires post-acquisition processing and can be prone to leaving some rare identifiable patients (for example, if the covariates include age, gender, and ethnicity, then a patient of very advanced age and known to be a patient at the specific customer hospital may be identifiable from the anonymized data).

Conversely, the CDS vendor may be unwilling to provide its proprietary CDS algorithm training procedure to the customer so as to enable the customer to perform the covariate shift adjustment using hospital patient data, because this training procedure may valuable trade secret information owned by the vendor.

Moreover, even if these logistical problems can be worked out so that the CDS algorithm can be updated to account for covariate shift (either at the vendor end or at the custom end), the customer is in the business of providing clinical care to patients and may be unable or ill-equipped to collect the requisite patient data to adjust for covariate shift.

In embodiments disclosed herein, these difficulties are overcome by performing the covariate shift update using population-level statistics for the individual covariates. These high-level statistics can be generated and distributed in reliably anonymized form, since they are not patient-specific data. The population-level covariate statistics can be viewed as marginal probability distributions for the various covariates. As disclosed herein, these marginal probability distributions are sufficient to provide covariate shift adjustment for a CDS device. Advantageously, this approach avoids collection (and distribution) of patient-level training samples that may be protected by patient privacy laws.

Moreover, in some embodiments the covariate shift adjustment is performed by way of training an additional covariate shift predictor that receives as input the prediction produced by the "stock" CDS algorithm trained at the CDS device vendor using the vendor's training data. The covariate shift predictor then outputs the covariate shift-adjusted prediction. In this way, the update can be performed at the customer end (e.g. at the hospital) without exposing the vendor's proprietary CDS algorithm training procedure to the customer. Since the covariate shift adjustment is expected to be a relatively small adjustment, the covariate shift adjustment predictor can employ logistic regression or another relatively simple predictor algorithm that is distributed to customers without concern about compromising proprietary trade secret information.

Figure 1:
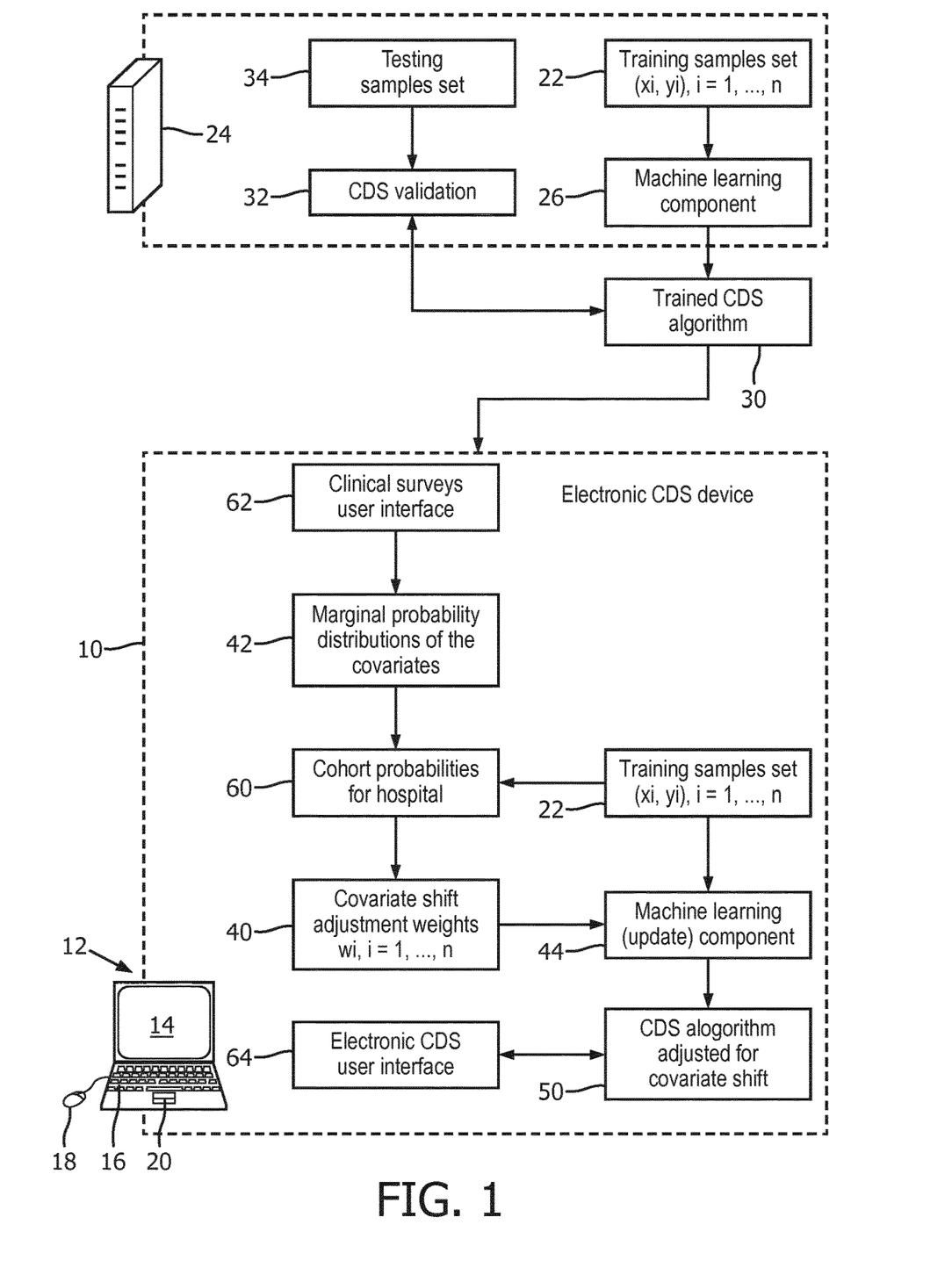
FIG. 1 diagrammatically shows an electronic clinical decision support (CDS) device including the manufacturing and the customer-side installation and user interfacing components.

With reference to FIG. 1, an electronic clinical decision support (CDS) device 10 includes a computer 12 with user interfacing components, e.g. an illustrative display 14 (for example, an LCD or plasma display monitor) and one or more user input devices (for example, an illustrative keyboard 16, an illustrative mouse 18 or trackpad 20 or other pointing device, a touchscreen overlay of the display 14, a voice recognition interface, various combinations thereof, or so forth). The illustrative computer is a desktop or notebook computer having a built-in processor performing computations entailed in implementing the CDS device; in other embodiments, a more decentralized computing architecture may be employed, e.g. the user interfacing components 14, 16, 18, 20 may be components of a "dumb" terminal that provides access to a remote server computer performing the CDS processing which is accessed via a hospital data network and/or the Internet, or in a still more decentralized architecture the CDS processing may be performed by a cloud computing resource or other distributed computing network—the term "computer" as used herein is intended to encompass all such distributed or decentralized computing systems as well as the illustrative centralized single-computer design.

The CDS device 10 employs a trained CDS algorithm that operates on values of covariates of a set of covariates to output a prediction of a medical condition. The trained CDS algorithm is initially trained on a training data set of training samples 22 using a computer 24, which is typically (although not necessarily) different from the computer 12. For example, in the illustrative example of a CDS provided by a vendor to a hospital or other customer, the computer 12 of the CDS device 10 may be the "customer" computer, and the computer 24 may be the "vendor" computer. In this context, the CDS device 10 performs "customer-side" processing, while the computer 24 performs "vendor-side' processing. This is merely an illustrative commercial model, and other types of commercialization are contemplated—for example, the computer 24 could be maintained by a hospital network, university, governmental agency or other large institution, while the CDS device 10 may be owned and/or maintained by a hospital, medical center, medical network, or the like.

The training data set of training samples 22 is denoted herein without loss of generality as a set $\{(x_i, y_i)\}_{i=1, \ldots, n}$ where n is the number of training samples (i.e. the number of training subjects), $x_i$ is the vector of covariate values for the $i^{th}$ training subject, and $y_i$ is the (known) value of the medical condition for the $i^{th}$ training subject. Again without loss of generality, the number of covariates in the set of covariates is denoted as m. The term "cohort" refers to a group of medical subjects having the same values for the covariates of the set of covariates. In some practical applications, each covariate has a binary value, in which case there are $2^m$ possible distinct combinations of covariates, i.e. $2^m$ possible cohorts. Binary-valued covariates are computationally convenient and can usefully represent numerous diagnostically valuable data items, such as the results of a medical test (positive or negative), the presence/absence of a condition (e.g., "1" indicating congestive heart failure, "0" indicating otherwise), and so forth. To be comprehensive, the training set 22 should include at least one patient belonging to each cohort; however, this is not required. Moreover, in some embodiments one or more of the covariates may not be binary-valued—e.g. an "age" covariate may have an integer value (age in years). One or more covariates may additionally/alternatively have other data types, e.g. a cancer grade covariate may assume an integer value in a range defined by the employed cancer-grading scheme. Likewise, the medical condition y to be predicted may be binary (e.g., the medical subject has the medical condition, or not) or may be more complex-valued (e.g. a cancer grade represented by an integer in accord with a cancer-grading scheme).

The vendor computer 24 is programmed to implement a machine learning component 26 that trains a clinical decision support (CDS) algorithm (or "predictor) 30 to operate on the values x of the covariates of the set of covariates to predict the medical condition y. Without loss of generality, the predictor 30 may be written as a prediction function $f(\ldots)$ operating on the set of covariate values x, that is, $y=f(x)$. In general, the machine learning component 26 employs an optimization algorithm to optimally predict the medical condition to be predicted for the training samples of the training set 22—these values are known a priori as the values $y_i$ of the training set, so the effectiveness of the predictor 30 can be quantitatively measured for the training set 22, e.g. using the normalized sum-squared error $$\frac{1}{N}\sum_{i=1}^{N}(\hat{y}_i - y_i)^2$$

where $\hat{y}_i = f(x_i)$ is the prediction provided by the predictor 30 for the $i^{th}$ training subject. The predictor 30 may in general employ any type of predictive function or algorithm, e.g. logistic regression, naïve Bayes, random forest, or so forth. Typically, the predictor 30 has a set of parameters whose values are optimized by the machine learning 26, e.g. using an iterative optimization process, to minimize the aforementioned normalized sum-squared error or other chosen objective.

In some embodiments, the training performed by the machine learning 26 may include selecting the covariates of the set of covariates using the training data set 22. For example, an initial (relatively large) set of covariates may be reduced to a smaller final set of covariates by applying a feature selection technique that retains the most relevant features, where "relevance" may be measured by a quantification such as mutual information. For example, Minimum-redundancy-maximum-relevance (mRMR) feature selection may be applied in some embodiments.

The vendor computer 24 may also be programmed to perform a validation process 32 to verify the accuracy of the trained CDS algorithm 30 to predict the medical condition for samples of a test samples set 34. To perform the validation, the test samples set 34 is also labeled, i.e. the ground-truth value y of the medical condition is known a priori for each test sample. In some embodiments, a cross-validation approach is used in which a single training set 22 is variously partitioned into training and testing sub-sets to perform the training and validation. It will be appreciated that the machine learning component 26 may be a commercially valuable trade secret developed and owned by the vendor, and as such the vendor may be unwilling to distribute this machine learning component 26 to third parties (such as customers) even in a compiled format. In other situations, the vendor may be willing to distribute this machine learning component 26, possibly with some protections such as a confidentiality agreement with the customer and/or other protections such as distributing the machine learning component 26 only in compiled format.

The customer is supplied with the trained CDS algorithm 30 and with the training data set 22, which is preferably anonymized to remove personally identifying information (PII). While the trained CDS algorithm 30 could be used directly for predicting the medical condition (y) in medical subjects (e.g. patients), this approach is susceptible to reduced accuracy due to covariate shift of the population served by the customer as compared with the population represented by the training data set 22. In illustrative embodiments herein, adjustment of the trained CDS algorithm 30 for covariate shift is performed using marginal probability distributions for the covariates of the set of covariates. Each marginal probability distribution is the probability distribution for one of the covariates of the set of covariates in the population served by the customer, without reference to any of the other covariates of the set of covariates. For example, if there are (again, without loss of generality) m covariates represented as $v_1, v_2, \ldots, v_m$, then these have a corresponding m marginal probability distributions $P_{cust}(v_1), P_{cust}(v_2), \ldots, P_{cust}(v_m)$ where the subscript $\bullet_{cust}$ indicates the marginal probabilities are for the population served by the customer. In illustrative embodiments herein, adjustment for covariate shift is performed by computing covariate shift adjustment weights 40 for the training samples of the training data set 22 using marginal probability distributions 42 for the covariates of the set of covariates, and performing update training on the training data set 22 with the training samples weighted by the covariate shift adjustment weights 40. In the illustrative embodiment, the update training is performed by a machine learning (update) component 44 executing on the customer-side computer 12—however, it is also contemplated for the update training to be performed at the vendor side, i.e. by the vendor computer 24. The output of the machine learning (update) component 44 is the trained CDS algorithm adjusted for covariate shift 50.

In illustrative embodiments described herein, a cohort of medical subjects is defined as a joint configuration over all covariates of the set of covariates. For example, consider the example in which the covariate shift adjustment is performed for only two covariates $v_1$ and $v_2$. (In general, the covariate shift may be performed for all covariates of the set of covariates, or for some chosen sub-set of the set of covariates). For illustrative purposes, the covariate $v_1$ is defined as a mechanical ventilation status, and is binary-valued: a medical subject is either on mechanical ventilation, or a medical subject is not on mechanical ventilation. The covariate $v_2$ is defined as sepsis status at time of admission to an Intensive Care Unit (ICU), and is again binary-valued: a medical subject either was septic when admitted to the ICU, or was not septic. With these two covariates, a total of four medical subject cohorts can be defined, which are listed in Table 1.

TABLE 1 illustrative set of cohorts for a set of two covariates

| Cohort | Ventilation status | Sepsis status at admission |
|---|---|---|
| 1 | Not mechanically ventilated | Not septic at admission |
| 2 | Not mechanically ventilated | Septic at admission |
| 3 | Mechanically ventilated | Not septic at admission |
| 4 | Mechanically ventilated | Septic at admission |

In general, m binary-valued covariates define $2^m$ cohorts of medical subjects. However, it will be appreciated that the disclosed covariate shift adjustment approaches are readily applied to CDS algorithms operating on a set of covariates that includes one, more, or even all covariates being capable of assuming more than two values, and/or being capable of assuming continuous values.

As previously noted, the training set 22 includes n samples (training subjects), each represented by a data pair $(x_i, y_i)$ where $x_i$ is the vector of values for the covariates of the set of covariates and $y_i$ is the known (ground truth) value of the medical condition to be predicted. Further, let $C_i$ denote the cohort of medical subjects to which the training example $(x_i, y_i)$ belongs.

Furthermore, let $P_{vendor}(C_i)$ denote the probability of cohort $C_i$ in the training set 22 employed by the vendor in training the CDS algorithm 30; and let $P_{cust}(C_i)$ denote the probability of cohort $C_i$ in the population served by the customer (e.g. hospital). Since the cohort $C_i$ is defined by the covariate values vector $x_i$ of the training subject (and does not depend on the value $y_i$ for the medical condition), it follows that the probability $P_{vendor}(C_i)$ is the joint probability of the covariate values stored in $x_i$ in the training data set 22; and likewise the probability $P_{cust}(C_i)$ is the joint probability of the covariate values stored in $x_i$ in the customer-side population. Using a standard covariate shift formulation, the covariate shift adjustment weight may be assigned to training example i as the ratio of these two probabilities:

$$w_i = \frac{P_{cust}(C_i)}{P_{vendor}(C_i)} \qquad (1)$$

Equation (1) assumes that the samples were not weighted during the vendor-side training performed to generate the trained CDS algorithm 30. On the other hand, the training samples may have been weighted during the vendor-side training. This may be done, for example, to introduce a desired bias to the CDS algorithm—as illustration, if it is preferred that the CDS algorithm tend to output a prediction that the medical subject has the medical condition in ambiguous cases, then this can be achieved by weighting positive samples (for which $y_i$ indicates the medical condition is present) relatively more than negative samples (for which $y_i$ indicates the medical condition is not present). If the weight applied to the $i^{th}$ during the vendor-side training of the CDS algorithm 30 is denoted as $\hat{w}_i$, the this can be accounted for by modifying Equation (1) as follows:

$$w_i = \frac{P_{cust}(C_i)}{P_{vendor}(C_i)} \cdot \hat{w}_i \qquad (2)$$

Since the training data set 22 is made available to the customer, estimation of the "vendor population" cohort statistics $P_{vendor}(C_1), P_{vendor}(C_2), \ldots, P_{vendor}(C_n)$ can be obtained from the statistics for these cohorts in the training data set 22. For example:

$$P_{vendor}(C_i) = \frac{n_{C_i}}{n} \qquad (3)$$

whereas used previously n is the total number of training samples in the training data set 22, and $n_{C_i}$ is the number of those training samples belonging to cohort $C_i$. It is apparent that $n_{C_i} \geq 1$ since at least the $i^{th}$ sample by definition belongs to cohort $C_i$, and for any useful training set $n_{C_i} < n$ since the training set 22 is constructed to contain training examples spanning the range of cohorts represented by the various combinations of permissible values of the covariates of the set of m covariates.

In the illustrative embodiment, the training data set 22 is made available to the customer, and the weights are computed at the customer-side, e.g. at the customer-side CDS device 10 in illustrative FIG. 1. In another embodiment, the customer is not provided with the training data set 22. In this variant embodiment, the marginal probability distributions $P_{cust}(v_1), P_{cust}(v_2), \ldots, P_{cust}(v_m)$ are provided by the customer to the vendor. This information is loaded to the vendor computer 24, and the covariate shift adjustment is performed at the vendor-side (e.g. by the vendor computer 24) as per Equations (1), (2), and/or (3). The model with the covariate shift adjustment is then communicated to the customer-side, e.g. loaded onto the CDS device 10. Thus, in these embodiments the covariate shift adjustment is performed by the vendor computer 24, rather than by the customer computer 12.

If an equivalent database of medical subjects fairly drawn from the customer-side population (e.g. the population of patients served by the ICU in this illustrative example) is available, then the customer-side analog of Equation (3) can be used to compute the probabilities $P_{cust}(C_i)$, and Equation (1) or (2) then applied to generate the weights. However, as previously noted, there are substantial problems with generating such a customer-side database, e.g. concerns about compromising patient privacy, difficulty in compiling such a database by a hospital that is in the business of providing clinical care rather than compiling statistical databases, and so forth. For the previous example, compiling such a customer-side database could only be done by an entity having authority to access the Electronic Medical Record (EMR) file of every patient entering the ICU, and the entity would need to have the (preferably automated) capability of mining the ventilator status and sepsis status at admission for each of these patients. It is noted that many practical CDS algorithms will operate on more than two covariates, and the covariates may be of diverse types, e.g. medical test results, pre-existing condition information, demographic data, and/or so forth.

In the illustrative embodiment of FIG. 1, the cohort probabilities $P_{cust}(C_1), \ldots, P_{cust}(C_n)$ 60 for the customer population are obtained from marginal probability distributions 42 for the individual covariates. Conceptually, if the marginal probabilities of the individual values of covariates that make up a cohort are high then the probability of that cohort should be high; conversely, if the marginal probabilities of the individual values of covariates that make up a cohort are low then the probability of that cohort should be low. To illustrate, if on average 95% of patients are mechanically ventilated, then we can infer that Cohorts 3 and 4 of Table 1 are much more likely than Cohorts 1 and 2.

Mathematically, inferring $P_{cust}(C_i)$ values from the marginal probabilities of the values of the defining covariates vector $x_i$ amounts to inferring a joint probability distribution over the m covariates from its m marginal probability distributions. In general, this is an underdetermined system with many possible solutions. To overcome this problem, the inference problem may optionally be regularized by finding the distribution $P_{cust}(C_i)$ that maximizes the effective sample size with respect to the training dataset 22. The effective sample size is a measure of the statistical power of the training dataset weighted by the weights of Equation (1) or (2). Maximizing effective sample size therefore increases the statistical power of estimators, such as machine learning classifiers, that are derived from the weighted training dataset 22. This has the benefit of reducing the risk of overfitting when update training the CDS algorithm 30 to adjust for covariate shift.

In a more specific illustrative approach, let $v_1, v_2, \ldots, v_m$, denote the m covariates that collectively define a cohort, so that each cohort $C_i$ may be represented by a particular joint configuration of values for the covariates $v_1, v_2, \ldots, v_m$. Further denote the marginal distributions as $P_{cust}(v_1), P_{cust}(v_2), \ldots, P_{cust}(v_m)$. The estimates for these marginal distributions may be denoted as $p_1, p_2, \ldots, p_m$, for example set $P_{cust}(v_1) = p_1$. By definition, the marginal distributions are computed by marginalizing out all other covariates in the joint distribution, so that constraining the marginal probabilities $P_{cust}(v_1), P_{cust}(v_2), \ldots, P_{cust}(v_m)$ to specified respective estimates $p_1, p_2, \ldots, p_m$ acts as direct constraints on the joint distribution. To estimate the joint distribution over cohorts $P_{cust}(C_i)$, the following optimization problem is solved:

$$\min_{P_{cust}} \sum_{\text{Training data: } (x_i, y_i, C_i)} \left( \frac{P_{cust}(C_i)}{P_{vendor}(C_i)} \right)^2 \quad (4)$$

subject to the following marginal probability estimate constraints:

$$P_{cust}(v_1) = p_1 \quad (5)$$
$$P_{cust}(v_2) = p_2$$
$$\vdots$$
$$P_{cust}(v_m) = p_m$$

In Equation (4), the notation $$\min_{P_{cust}} \sum \ldots$$

indicates that the cohort probabilities $P_{cust}(C_i)$ are optimized to minimize the value of the summation (subject to the constraints set forth in Equation (5)). It can be shown that the optimization problem of Equations (4) and (5) maximizes the effective sample size subject to the marginal distribution constraints of Equation (5). This optimization problem is convex so it is efficient to solve for the unique globally optimal solution.

From the optimization of Equations (4) and (5), the cohort probabilities 60 (i.e. probabilities $P_{cust}(C_1), P_{cust}(C_2), \ldots, P_{cust}(C_n)$) are inferred. The corresponding covariate shift adjustment weighting values 40 (i.e., weights $w_1, w_2, \ldots, w_n$) are then computed from Equation (1) or (2). As seen in FIG. 1, these weights are then fed into the machine learning update component 44 along with the original training dataset 22. The output of this training component 44 is the trained CDS algorithm adjusted for covariate shift 50.

The foregoing assumes availability of the marginal probability distributions $P_{cust}(v_1) = p_1, P_{cust}(v_2) = p_2, \ldots, P_{cust}(v_m) = p_m$. In the illustrative embodiment, these marginal probability distributions are obtained from answers to clinical survey questions completed by hospital personnel (or, more generally, by the customer or a customer agent) using a clinical surveys user interface 62 provided by the CDS device 10. For the example of Table 1, a clinical survey could, for example, be formulated as a two-question survey:
1. On average, what percentage of patients are on mechanical ventilation?
2. On average, what percentage of patients have sepsis when admitted to the ICU?

For covariates that are not binary-valued, the survey questions may be formatted accordingly. For example, a lung cancer staging covariate may be an input to a CDS algorithm for indicating whether radiation therapy is indicated. The survey question for obtaining data to generate the marginal probability distribution for the lung cancer staging covariate may be suitably expressed as follows:

Please indicate the percentage of lung cancer patients in each of the following cancer stages (the percentages should add up to 100%):
Stage 0 ______%
Stage I ______%
Stage II ______%
Stage III ______%
Stage IV ______%

The clinical surveys user interface 62 preferably performs a data check on the percentage values to ensure the fractions add up to 100%.

In general, the clinical surveys user interface 62 may utilize the display 14 to present survey questions to the customer or customer agent, and may utilize the one or more user input devices 16, 18, 20 to receive responses from the customer/agent, e.g. by having them typed via the keyboard 16 or by moving sliders running from 0%-100% using a pointing device 18, 20. Advantageously, the clinical survey questions collect "coarse" statistics, that is, population-level statistics for the hospital or other customer. The answers to these survey questions do not contain individual patient-level information, and hence do not include patient-identifying information (PII). Accordingly, the clinical survey questions generally do not raise patient privacy concerns. Furthermore, the covariate shift adjustment can be usefully performed even if the marginal probability distributions are only approximate—hence, it may be sufficient to obtain answers to the survey questions that are only approximate, e.g. even if the customer or customer agent (e.g. nurse, ICU department direct, or so forth) does not have exact information, it may be sufficient to provide estimates. For example, the customer agent may estimate that 20% of patients have sepsis when admitted to the ICU—even if the exact percentage is slightly different (e.g. 15%, or 30%), the covariate adjustment may still be useful to correct for a covariate shift if (for example) 50% of patient have sepsis when entering the ICU in the case of the vendor training data 22.

With the covariate shift update completed, a prediction of the medical condition for a medical subject may be generated by applying the trained CDS algorithm adjusted for covariate shift 50 to values for the medical subject of the covariates of the set of covariates. To this end, an electronic CDS user interface 64 is provided, by which a doctor, nurse, or other medical professional may enter values of the covariates for the patient (e.g. using the one or more user input devices 16, 18, 20) and the prediction of the medical condition may be presented, e.g. by being displayed on the display 14. Depending upon the connectivity of the CDS device 10, some of the covariate values may be obtained automatically by accessing the medical subject's Electronic Medical Record (EMR) file, thereby reducing the amount of manual data entry required. In some embodiments, the CDS device 10 may be programmed to compute or derive one or more of the covariate values from other information, e.g. the determination of sepsis at time of admission to the ICU may be made based on analysis of vital sign measurements of the patient at the time of admission.

In the following, some illustrative embodiments of the machine learning update component 44 that performs the covariate shift adjustment are described. In one approach, the machine learning update component 44 is a copy of the machine learning component 26 that executes on the vendor computer 24 to generate the trained CDS algorithm 30. In this approach, the CDS algorithm itself is updated. The update training suitably uses the parameters of the trained CDS algorithm 30 as initial parameter values, and since the impact of covariate shift is expected to be relatively small these initial parameters are expected to be good starting values for the update training, thus allowing the CDS algorithm update training to be performed on the customer computer 12 in a few iterations. For this approach, the training process employed by the machine learning component 26 needs to accept weights for the data samples of the data set 22 (or, alternatively, the copy running on the customer computer 12 is modified to accept these weight). Furthermore, this requires that the vendor be willing to supply an executable version of its machine learning component 26 to each CDS device customer. If the learning component 26 is considered trade secret or otherwise confidential information, then the vendor may be unwilling to share the learning component 26 with customers.

Figure 2:
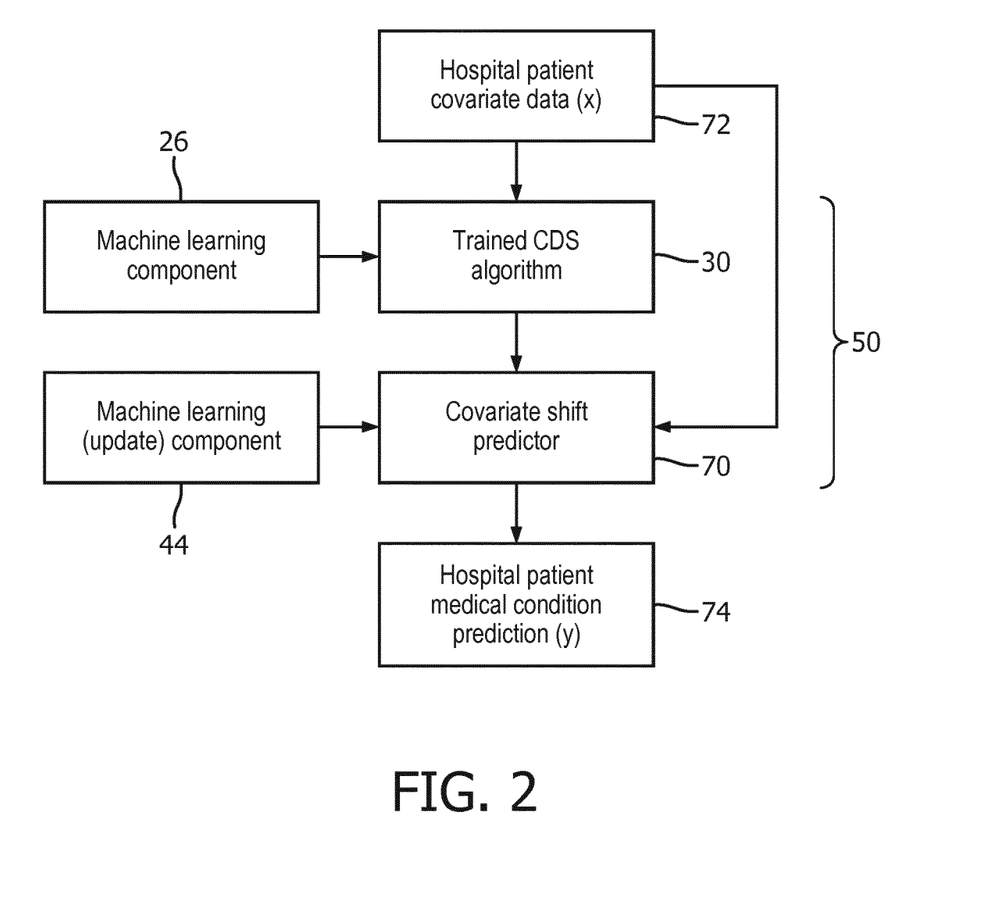
FIG. 2 diagrammatically shows an implementation of the electronic CDS device of FIG. 1 employing a vendor-trained CDS medical condition prediction algorithm and a customer-trained covariate shift predictor.

With continuing reference to FIG. 1 and with further reference to FIG. 2, an alternative approach is disclosed which allows for updating the trained CDS algorithm 30 to adjust for covariate shift at the customer end, without the need to share the learning component 26 with customers. In this approach, the trained CDS algorithm adjusted for covariate shift 50 includes (as shown in FIG. 2): (i) the trained CDS algorithm 30 that was trained by the machine learning component 26 executing on the vendor computer 24, and (ii) a covariate shift predictor 70 trained by the machine learning update component 44 executing on the customer computer 12 that operates on the prediction of the medical condition output by the trained CDS algorithm 30. Thus, as shown in FIG. 2, during the inference phase the values of covariates (x) for the medical subject 72 under diagnosis by the customer are input to the trained CDS algorithm 30 operated to output the prediction, and this prediction is then input to the covariate shift predictor 70 to generate the prediction (y) for the medical subject 74. In this embodiment, the machine learning update component 44 performs update training by training the covariate shift predictor 70 on the training data set 22 with the training samples weighted by the covariate shift adjustment weights 40, and this training of the covariate shift predictor 70 does not modify the trained CDS algorithm 30 provided by the vendor. As a consequence, there is no need for the customer to have access to the (potentially proprietary) machine learning component 26 of the vendor. Moreover, because the covariate shift is expected to be relatively small, the covariate shift predictor 70 can be relatively computationally simple. For example, in some embodiments the covariate shift predictor 70 comprises a logistic regression predictor.

Figure 3:
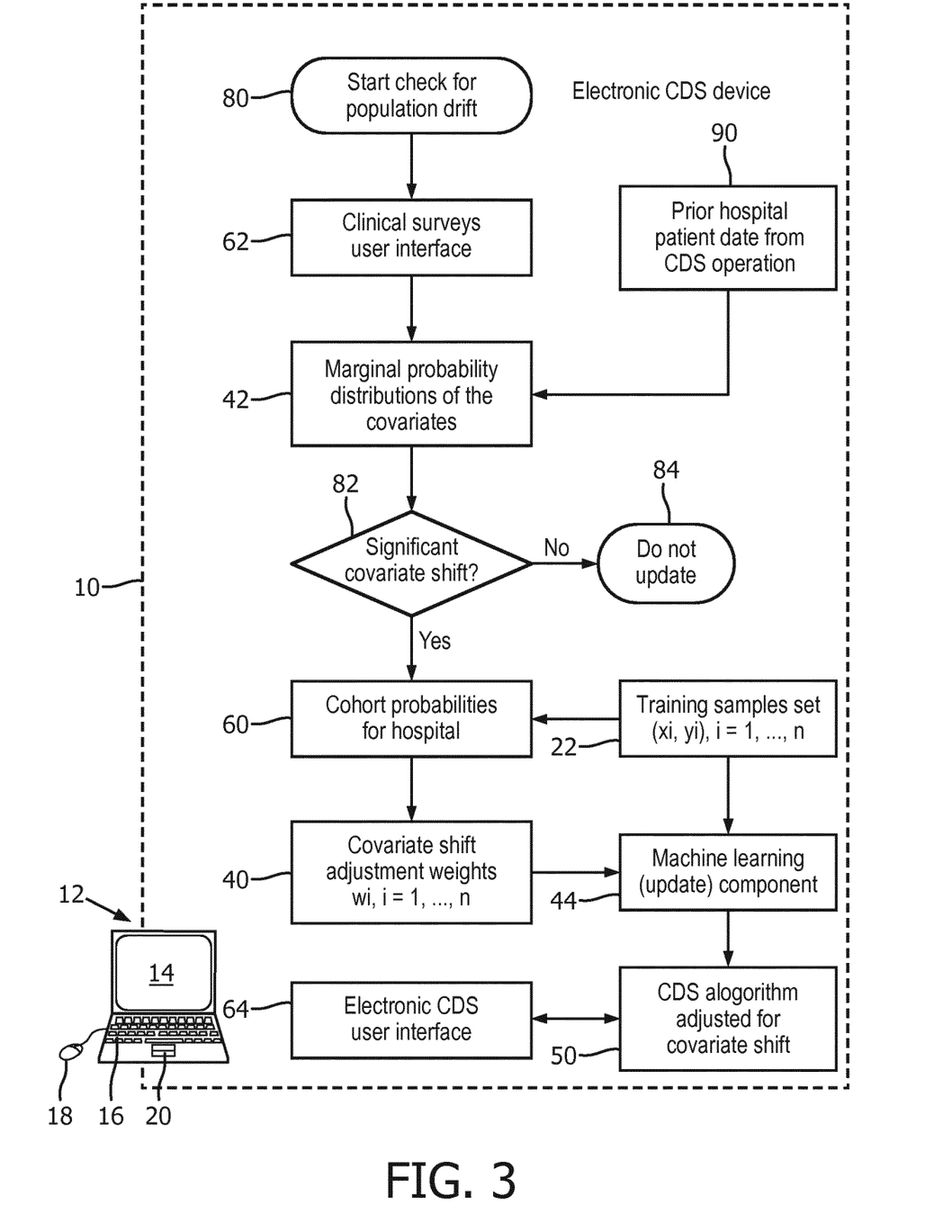
FIG. 3 diagrammatically shows the electronic CDS device of FIG. 1 including a covariant shift adjustment update feature.

With reference to FIG. 3, the covariate shift adjustment may be repeated occasionally in order to account for changes over time in medical subject demographics or other shifts over time in the covariate statistics at the customer end. For example, FIG. 3 illustrates that such a check is initiated by a trigger 80 which may be, for example, an annual check for population shifts, and/or the trigger 80 may be on some other basis such as the closing of a nearby hospital and consequent influx of patients that were previously treated at the now-closed neighboring hospital. The trigger 80 leads to re-presenting the clinical survey questions by the user interface 62, and generation of the marginal probability distributions 42. These may then be compared with the marginal probability distributions generated during the last covariate shift adjustment. In a decision 82, if the changes in marginal probability distributions are below some threshold value then the check is terminated at 84 without performing an update covariate shift adjustment. On the other hand, if one or more marginal probability distributions has changed significantly, the cohort probabilities 60 and weights 40 are recalculated, and the machine learning update component 44 is invoked to perform an update covariate shift adjustment as already described with reference to FIG. 1.

In the embodiment of FIG. 1, the marginal probability distributions are generated from answers to survey questions presented to the customer or customer agent using the clinical surveys user interface 62. In particular, in some embodiments the update training to adjust for covariate shift does not use any training samples other than the training data set 22 of training samples.

However, additional and/or other sources of information may be used for generating the marginal probability distributions. For example, with reference to FIG. 3, as the electronic CDS user interface 64 is employed to perform medical subject diagnoses, the CDS device 10 can collect information on medical subjects that are diagnosed. As each of these medical subjects is represented by the set of values (x) of the covariates for that medical subject, these accumulated data may be used to construct a data set 90 that is representative of the customer-side population. The data set 90 may be used to estimate the marginal probability distributions, e.g. the probability of a value v for a covariate is given by:

$$P_{cust}(v) = \frac{N_v}{N} \quad (6)$$

where N is the total number of medical subjects in the data set 90, and $N_v$ is the number of those medical subjects having the value v for the covariate. This data may then be used as the marginal probability distributions 42 of the covariates.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An electronic clinical decision support (CDS) device employing a trained CDS algorithm that operates on values of covariates of a set of covariates to output a prediction of a medical condition, the trained CDS algorithm having been trained on a training data set of training samples from a training population, the electronic CDS device comprising: a computer including a display and one or more user input devices, the computer programmed to:
receive, via the one or more user input devices, responses to one or more survey questions from a user, wherein the survey questions are configured to collect population-level statistics in anonymized form regarding a population different from the training population used for training the CDS algorithm, such that the population-level statistics do not contain patient-level information;
generate marginal probability distributions for the covariates of the set of covariates using the population-level statistics, wherein the marginal probability distributions correspond to probability distributions for the covariates of the set of covariates in the population different from the training population used for training the CDS algorithm;
compute covariate shift adjustment weights for the training samples of the training data set using the marginal probability distributions for the covariates of the set of covariates;
perform update training on the training data set by a machine learning algorithm with the training samples weighted by the covariate shift adjustment weights;
adjust the trained CDS algorithm for covariate shift using the updated training data set;
generate a prediction of the medical condition for a medical subject to provide clinical diagnostic assistance by applying the trained CDS algorithm adjusted for covariate shift to values for the medical subject of the covariates of the set of covariates; and
display the generated prediction of the medical condition for the medical subject on the display,
wherein computing the covariate shift adjustment weights for the training samples of the training data set using the marginal probability distributions includes:
optimizing joint probability distributions over the set of covariates with respect to the training data set constrained by the marginal probability distributions for the covariates of the set of covariates; and
computing the covariate shift adjustment weights for the training samples of the training data set from the optimized joint probability distributions.

2. The electronic CDS device of claim 1 wherein:
the machine learning algorithm comprises a covariate shift predictor that operates on the prediction of the medical condition output by the trained CDS algorithm and the values of covariates on which the trained CDS algorithm operated to output the prediction; and
performing update training comprises training the covariate shift predictor on the training data set with the training samples weighted by the covariate shift adjustment weights, wherein the training of the covariate shift predictor does not modify the trained CDS algorithm.

3. The electronic CDS device of claim 2 wherein the covariate shift predictor comprises a logistic regression predictor.

4. The electronic CDS device of claim 1 wherein the adjustment of the trained CDS algorithm for covariate shift does not use any training samples other than the training data set of training samples.

5. The electronic CDS device of claim 1, wherein optimizing the joint probability distributions includes maximizing an effective sample size of the training data set.

6. The electronic CDS device of claim 1 wherein the trained CDS algorithm is adjusted for covariate shift without using any training samples other than the training data set of training samples.

7. An electronic clinical decision support (CDS) method employing a CDS algorithm that operates on values of covariates of a set of covariates to output a prediction of a medical condition, the electronic CDS method comprising:

training the CDS algorithm on a training data set of training samples from a training population using a first computer;

after the training, performing CDS operations using a second computer different from the first computer, the CDS operations including:

receiving, via the one or more user input devices, responses to one or more survey questions from a user, wherein the survey questions are configured to collect population-level statistics in anonymized form, such that the population-level statistics do not contain patient-level information;

generating marginal probability distributions for the covariates of the set of covariates using the population-level statistics, wherein the marginal probability distributions correspond to probability distributions for the covariates of the set of covariates in a population different from the training population used for training the CDS algorithm:

computing covariate shift adjustment weights for the training samples of the training data set using the marginal probability distributions;

performing update training on the training data set by a machine learning algorithm with the training samples weighted by the covariate shift adjustment weights;

adjusting the trained CDS algorithm for covariate shift using the updated training data set;

generating a prediction of the medical condition to provide clinical diagnostic assistance for a medical subject by applying the trained CDS algorithm adjusted for covariate shift to values for the medical subject of the covariates of the set of covariates; and displaying the generated prediction of the medical condition for the medical subject on a display, wherein computing the covariate shift adjustment weights for the training samples of the training data set includes:

optimizing joint probability distributions over the set of covariates with respect to the training data set constrained by the marginal probability distributions for the covariates of the set of covariates; and computing the covariate shift adjustment weights for the training samples of the training data set from the optimized joint probability distributions.

8. The electronic CDS method of claim 7, wherein optimizing the joint probability distributions includes maximizing an effective sample size of the training data set.

9. The electronic CDS method of claim 7, wherein:

the trained CDS algorithm adjusted for covariate shift comprises the trained CDS algorithm and a covariate shift predictor that operates on the prediction of the medical condition output by the trained CDS algorithm and the values of covariates on which the trained CDS algorithm operated to output the prediction; and performing update training comprises training the covariate shift predictor on the training data set with the training samples weighted by the covariate shift adjustment weights wherein the training of the covariate shift predictor does not modify the trained CDS algorithm.

10. The electronic CDS method of claim 7 wherein the trained CDS algorithm is adjusted for covariate shift without using any training samples other than the training data set of training samples.

11. The electronic CDS method of claim 7 wherein the training includes selecting the covariates of the set of covariates using the training data set.

12. An electronic clinical decision support (CDS) device, comprising:

a processor;

a non-transitory memory that stores instructions that, when executed by the processor, cause the processor to:

receive a trained CDS algorithm that operates on values of covariates of a set of covariates to output a prediction of a medical condition, wherein the trained CDS algorithm has been trained on a training data set of training samples from a training population;

receive, via the one or more user input devices, responses to one or more survey, questions from a user, wherein the survey questions are configured to collect population-level statistics in anonymized form, such that the population-level statistics do not contain patient-level information;

generate marginal probability distributions for the covariates of the set of covariates using the population-level statistics, wherein the marginal probability distributions correspond to probability distributions for the covariates of the set of covariates in a population different from the training population used for training the CDS algorithm;

compute covariate shift adjustment weights for the training samples of the training data set using the marginal probability distributions for the covariates of the set of covariates by optimizing joint probability distributions over the set of covariates with respect to the training data set constrained by the marginal probability distributions for the covariates of the set of covariates, and computing the covariate shift adjustment weights for the training samples of the training data set from the optimized joint probability distributions;

perform update training on the training data set by a machine learning algorithm with the training samples weighted by the covariate shift adjustment weights;

adjust the trained CDS algorithm for covariate shift using the updated training data set;

generate a prediction of the medical condition for a medical subject to provide clinical diagnostic assistance to a medical professional by applying the trained CDS algorithm adjusted for covariate shift to values for the medical subject of the covariates of the set of covariates; and display the generated prediction of the medical condition for the medical subject.

* * * * *